US012580042B2

(12) United States Patent
Wu et al.

(10) Patent No.: US 12,580,042 B2
(45) Date of Patent: Mar. 17, 2026

(54) LIGAND SCREENING MODEL CONSTRUCTION METHOD AND DEVICE, A SCREENING METHOD, A DEVICE, AND A MEDIUM

(71) Applicant: Ainnocence Technologies LLC, Miami, FL (US)

(72) Inventors: Junfeng Wu, Shanghai (CN); Yutong Jin, Zhengzhou (CN); Lurong Pan, Vestavia Hill, AL (US)

(73) Assignee: Ainnocence Technologies LLC

( * ) Notice: Subject to any disclaimer, the term of this patent is extended or adjusted under 35 U.S.C. 154(b) by 844 days.

(21) Appl. No.: 17/931,917

(22) Filed: Sep. 14, 2022

(65) Prior Publication Data

US 2023/0402135 A1    Dec. 14, 2023

(51) Int. Cl.
| | |
|---|---|
| *G16B 15/30* | (2019.01) |
| *G06N 3/04* | (2023.01) |
| *G06N 3/08* | (2023.01) |
| *G16C 20/50* | (2019.01) |
| *G16C 20/70* | (2019.01) |
| *G16C 20/80* | (2019.01) |
| *G16C 10/00* | (2019.01) |
| *G16C 20/30* | (2019.01) |

(52) U.S. Cl.
CPC .............. *G16B 15/30* (2019.02); *G06N 3/04* (2013.01); *G06N 3/08* (2013.01); *G16C 20/50*

(2019.02); *G16C 20/70* (2019.02); *G16C 20/80* (2019.02); *G16C 10/00* (2019.02); *G16C 20/30* (2019.02)

(58) Field of Classification Search
USPC .......................................................... 702/22
See application file for complete search history.

(56) References Cited

U.S. PATENT DOCUMENTS

| | | | | |
|---|---|---|---|---|
| 11,256,994 | B1 * | 2/2022 | Bucher ................. | G06V 20/69 |
| 2018/0204111 | A1 * | 7/2018 | Zadeh ................. | G06V 10/764 |
| 2020/0342953 | A1 * | 10/2020 | Morrone ............... | G16B 20/30 |
| 2021/0142173 | A1 * | 5/2021 | Cheng ..................... | G06N 3/08 |
| 2022/0358373 | A1 * | 11/2022 | Bucher ................. | G16C 20/50 |

* cited by examiner

*Primary Examiner* — Paul D Lee
(74) *Attorney, Agent, or Firm* — Jason C. Cameron

(57) ABSTRACT

A ligand screening model construction method, a ligand screening model construction device, and a drug ligand screening method for drug screening, comprising that obtain a drug ligand training set, and the drug ligand training set includes a drug ligand chemical formula and a classification label; a ligand graph network is drawn, in which atoms are nodes and chemical bonds are edges connecting nodes; use a random initialization vector to identify the weight vector of each node in the ligand graph network; reconstruct each node of the ligand graph network to obtain a reconstruction network, and repeat the reconstruction steps to obtain at least two layers of reconstruction networks; perform deep learning on the ligand graph network and the at least two-layer reconstruction graph network according to the classification labels, and construct a ligand screening model.

17 Claims, 4 Drawing Sheets

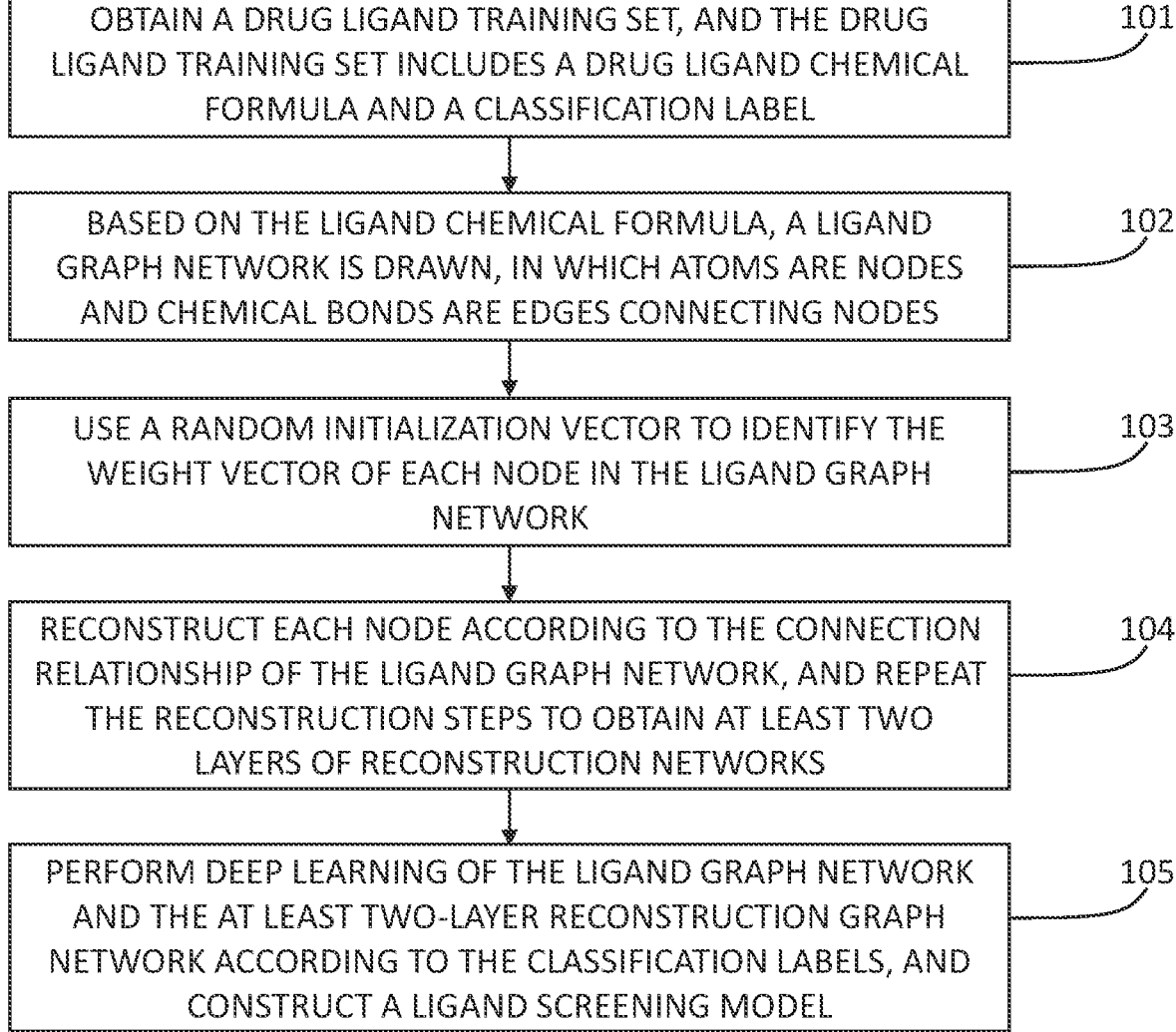

OBTAIN A DRUG LIGAND TRAINING SET, AND THE DRUG LIGAND TRAINING SET INCLUDES A DRUG LIGAND CHEMICAL FORMULA AND A CLASSIFICATION LABEL — 101

BASED ON THE LIGAND CHEMICAL FORMULA, A LIGAND GRAPH NETWORK IS DRAWN, IN WHICH ATOMS ARE NODES AND CHEMICAL BONDS ARE EDGES CONNECTING NODES — 102

USE A RANDOM INITIALIZATION VECTOR TO IDENTIFY THE WEIGHT VECTOR OF EACH NODE IN THE LIGAND GRAPH NETWORK — 103

RECONSTRUCT EACH NODE ACCORDING TO THE CONNECTION RELATIONSHIP OF THE LIGAND GRAPH NETWORK, AND REPEAT THE RECONSTRUCTION STEPS TO OBTAIN AT LEAST TWO LAYERS OF RECONSTRUCTION NETWORKS — 104

PERFORM DEEP LEARNING OF THE LIGAND GRAPH NETWORK AND THE AT LEAST TWO-LAYER RECONSTRUCTION GRAPH NETWORK ACCORDING TO THE CLASSIFICATION LABELS, AND CONSTRUCT A LIGAND SCREENING MODEL — 105

FIG. 1

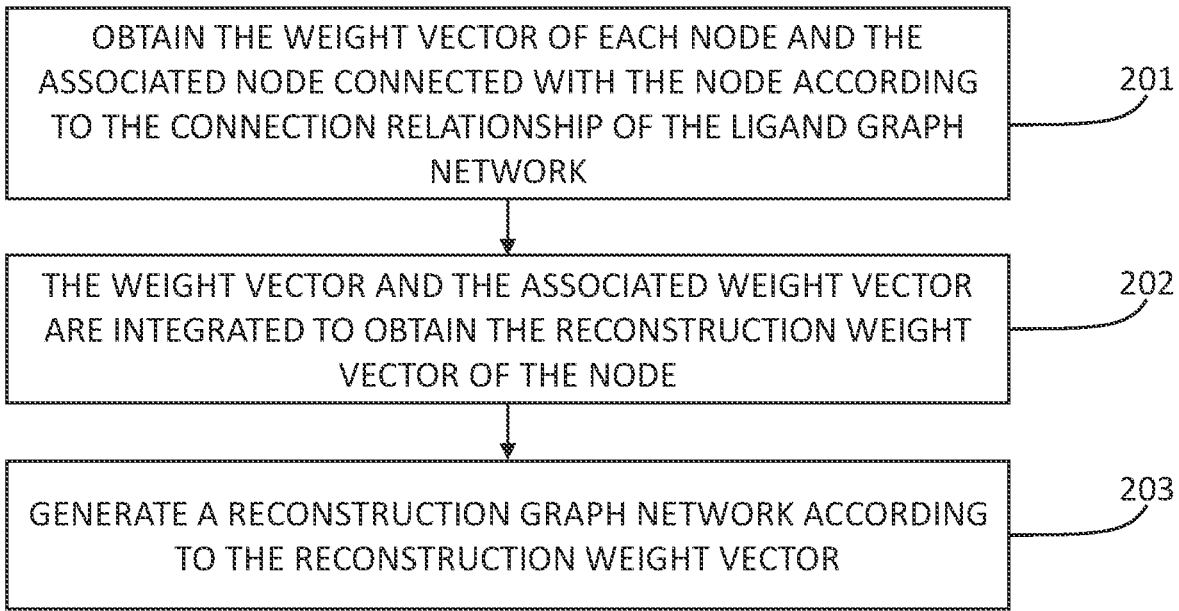

OBTAIN THE WEIGHT VECTOR OF EACH NODE AND THE ASSOCIATED NODE CONNECTED WITH THE NODE ACCORDING TO THE CONNECTION RELATIONSHIP OF THE LIGAND GRAPH NETWORK — 201

THE WEIGHT VECTOR AND THE ASSOCIATED WEIGHT VECTOR ARE INTEGRATED TO OBTAIN THE RECONSTRUCTION WEIGHT VECTOR OF THE NODE — 202

GENERATE A RECONSTRUCTION GRAPH NETWORK ACCORDING TO THE RECONSTRUCTION WEIGHT VECTOR — 203

FIG. 2

A TRAINING SET ACQUISITION MODULE   301

A GRAPH NETWORK DRAWING MODULE   302

A VECTOR IDENTIFICATION MODULE   303

A RECONSTRUCTION MODULE   304

A MODEL TRAINING MODULE   305

LIGAND SCREENING MODEL CONSTRUCTION METHOD AND DEVICE, A SCREENING METHOD, A DEVICE, AND A MEDIUM

CROSS REFERENCE TO RELATED APPLICATIONS

This application claims priority from a patent application filed in China having Patent Application No. 2022106542677 filed on Jun. 12, 2022, and titled "A LIGAND SCREENING MODEL CONSTRUCTION METHOD AND DEVICE, A SCREENING METHOD, A DEVICE, AND A MEDIUM".

TECHNICAL FIELD OF THE INVENTION

The invention relates to the field of drug screening, in particular to a ligand screening model construction method, a ligand screening model construction device, a drug ligand screening method, a device and a medium.

BACKGROUND OF THE INVENTION

Drug discovery has long been a process that consumes a lot of time and money. With the development of computer technology, computational methods are widely used in drug research and development, and virtual drug screening is one of the most valuable technologies.

In drug discovery and virtual screening, draw the structural or functional similarity of chemical molecules by analyzing molecular fingerprints. However, the existing molecular fingerprint generation methods rely on the manual feature extraction of developers, which puts forward high requirements for developers. Developers need to have a deep understanding of domain knowledge, otherwise it is not conducive to the subsequent virtual screening or drug discovery.

SUMMARY OF THE INVENTION

Therefore, in order to overcome the above-mentioned shortcomings of the prior art, the present invention provides a ligand screening model construction method, a ligand screening model construction device, a drug ligand screening method, a device and a medium which can accurately predict the properties of compounds in biological and chemical experiments of different scales.

In order to achieve the above object, the present invention provides a ligand screening model construction method, which comprises: obtain a drug ligand training set, and the drug ligand training set includes a drug ligand chemical formula and a classification label; based on the ligand chemical formula, a ligand graph network is drawn, in which atoms are nodes and chemical bonds are edges connecting nodes; use a random initialization vector to identify the weight vector of each node in the ligand graph network; reconstruct each node of the ligand graph network according to the connection relationship of the ligand graph network to obtain a reconstruction network, and repeat the reconstruction steps to obtain at least two layers of reconstruction networks; perform deep learning on the ligand graph network and the at least two-layer reconstruction graph network according to the classification labels, and construct a ligand screening model.

In one of the embodiments, using random initialization vector to identify the weight vector of each node in the ligand graph network includes: using uniform distribution or normal distribution to select the value of (0,1) interval to generate initialization vector, and assigning it to the node as its weight vector.

In one of the embodiments, reconstructing each node of the ligand graph network according to the connection relationship of the ligand graph network to obtain a reconstruction network includes: obtain the weight vector of each node and the associated weight vector of the associated node connected with the node according to the connection relationship of the ligand graph network; integrate the weight vector and the associated weight vector to obtain the reconstruction weight vector of the node; generate a reconstruction network according to the reconstruction weight vector.

In one of the embodiments, the ligand graph network and at least two layers of reconstruction graph networks are deeply learned according to the classification labels, and construct a ligand screening model, which includes: respectively extracting the features of the ligand graph network and the at least two layers of reconstruction graph networks to obtain hierarchical network features; According to the classification label, a deep learning network is adopted to learn the hierarchical network characteristics, and construct a ligand screening model.

In one of the embodiments, feature extraction is performed on the ligand graph network and the at least two-layer reconstruction graph network respectively to obtain hierarchical network features, including: performing feature extraction on the ligand graph network and the at least two layers of the reconstruction graph network respectively through a function to obtain function vector features; The function vector features are normalized in probability space to obtain hierarchical network features.

A drug ligand screening method, including:

Drawing a target ligand graph network based on the ligand chemical formula of the target ligand, in which atoms are nodes and chemical bonds are edges connecting the nodes; input the target ligand graph network into the ligand screening model, and output the analysis result of the target ligand, wherein the ligand screening model is trained by the above method.

A ligand screening model construction device is provided, which includes: a training set acquisition module, configured to acquire a drug ligand training set, wherein the drug ligand training set includes a drug ligand chemical formula and a classification label; a network drawing module is used to draw a ligand graph network based on the ligand chemical formula, in which atoms are nodes and chemical bonds are edges connecting nodes; a vector identification module is configured to identify the weight vector of each node in the ligand graph network by using a random initialization vector; a reconstruction module is used to reconstruct each node of the ligand graph network according to the connection relationship of the ligand graph network to obtain a reconstruction graph network, and repeating the reconstruction steps to obtain at least two layers of reconstruction networks; a model training module is used for deeply learning the ligand graph network and at least two layers of reconstruction graph networks according to the classification labels, and construct a ligand screening model.

A computer device comprises a memory and a processor, wherein the memory stores a computer program, and is characterized in that the processor implements the steps of the above method when executing the computer program.

A computer readable storage medium, on which a computer program is stored, is characterized in that when a processor execute the computer program, implementing the steps of the above method.

Compared with the prior art, the present invention has the advantages that by modeling and analyzing the ligand graph network corresponding to the ligand chemical formula, and adopting the ligand graph network and the reconstruction graph network in modeling instead of the traditional mode based on molecular fingerprint (Fingerprint), can identify two different graph networks of the same ligand only by machine learning, which can not only effectively reduce artificial feature design, but also expand the coverage of features, improve efficiency and accuracy, And by using big data and deep learning methods, greatly save the computational consumption of molecular dynamics, quantum mechanics, quantum chemistry, etc., and greatly improve the computational speed. The present invention can better simulate the structural diversity of small molecules in different physiological environments, and accurately predict the properties of compounds in biological and chemical experiments of different scales.

BRIEF DESCRIPTION OF DRAWINGS

In order to illustrate the technical solutions of the embodiments of the present application more clearly, the following briefly introduces the drawings that are used in the embodiments.

Obviously, the drawings in the following description are only some embodiments of the present application, and for persons skilled in the art, other drawings may also be obtained according to the drawings without any creative efforts.

FIG. 1 is a schematic flowchart of a ligand screening model construction method in an embodiment of the present invention;

FIG. 2 is a schematic flowchart of a reconstruction step in an embodiment of the present invention;

DETAILED DESCRIPTION

Figure 3:
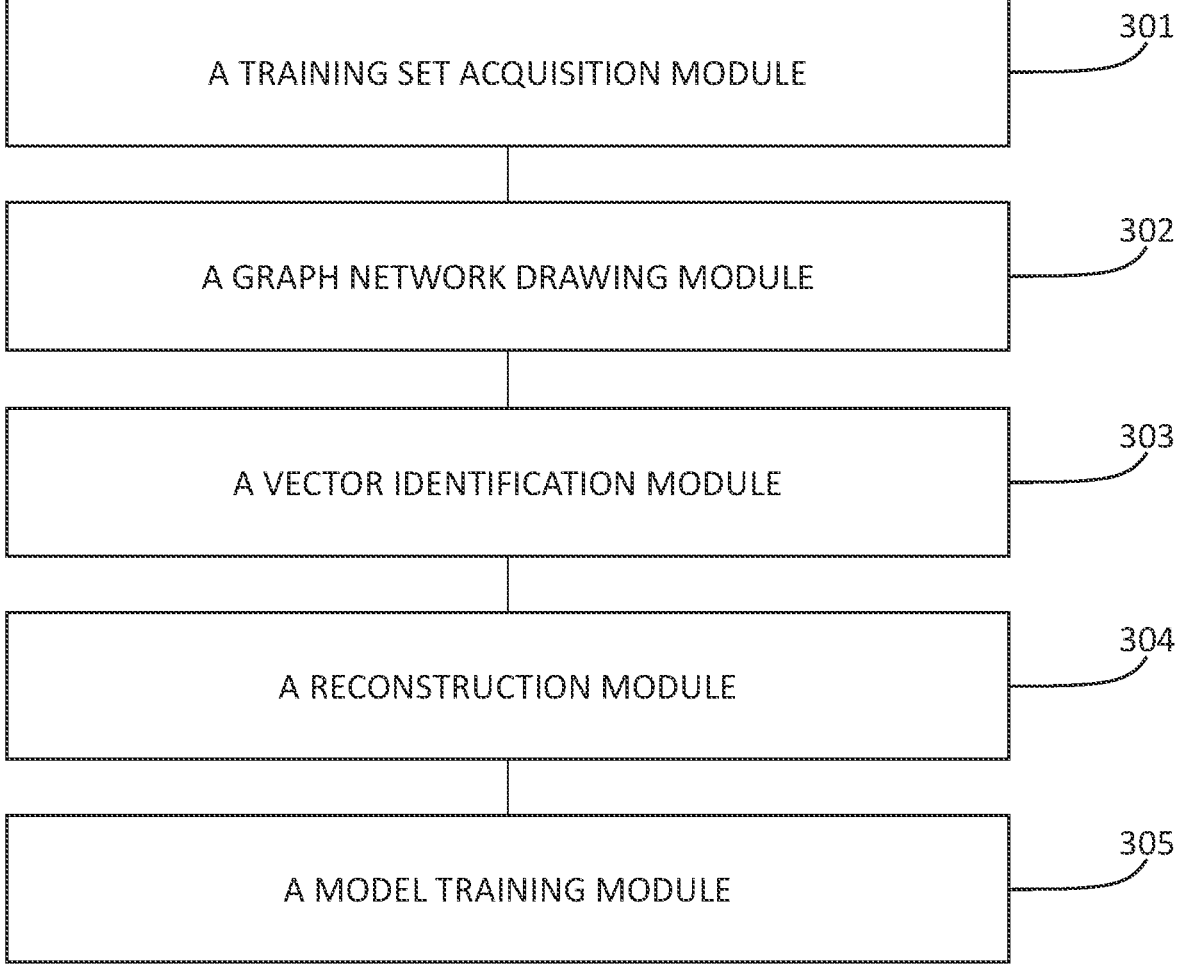
FIG. 3 is the structural block diagram of the ligand screening model construction device in the embodiment of the present invention.

The embodiments of that present disclosure are described in detail below with reference to the drawings.

The embodiments of the present disclosure are described below by way of specific examples, and those skilled in the art can easily understand other advantages and effects of the present disclosure from the contents disclosed in this specification. Obviously, the described embodiments are only a part of the embodiments of the present disclosure, but not all of the embodiments. The present disclosure may be implemented or applied by different other embodiment, and that details of the present specification may be modified or changed from various aspect and applications without departing from the spirit of the present application. It should be noted that the following embodiments and the features in the embodiments can be combined with each other without conflict. Based on the embodiments in the present disclosure, all other embodiments obtained by persons of ordinary skill in the art without creative work are within the scope of the protection of the present disclosure.

It should be noted that various aspects of embodiments within the scope of the appended claims are described below. It should be apparent that the aspects described herein may be embodied in a wide variety of forms, and that any specific structures and/or functions described herein are merely illustrative. Based on the present application, persons skilled in the art will appreciate that one aspect described herein may be implemented independently of any other aspect and that two or more of these aspects may be combined in various ways. For example, any number and aspects set forth herein may be used to implement an apparatus and/or practice a method. In addition, the apparatus may be implemented and/or the method practiced using other structures and/or functionalities in addition to one or more of the aspects set forth herein.

It is to be noted that, various aspects of embodiments within the scope of the appended claims are described below. It is obvious that the aspects described herein can be embodied in a wide variety of forms, and any specific structures and/or functions described herein are illustrative only. Based on this disclosure, persons skilled in the art should understand that one aspect described herein can be implemented independently of any other aspect, and two or more of these aspects can be combined in various ways. For example, any number of aspects set forth herein can be used to implement devices and/or practice methods. In addition, other structures and/or functionalities other than one or more of the aspects set forth herein can be used to implement this device and/or practice this method.

It should also be noted that the illustrations provided in the following examples illustrate the basic concepts of the present application by way of illustration only. The drawings only show the components related to the present application and are not drawn according to the number, shape and size of the components in the actual implementation. The type, number and proportion of each component in the actual implementation may be changed at will, and the layout type of the components may be more complicated.

Furthermore, details in the following description are for a purpose of a thorough understanding of the embodiments. However, it is to be understood by those skilled in the art that an aspect of the disclosure may be practiced without these details.

As shown in FIG. 1, an embodiment of the present disclosure provides a method for constructing a ligand screening model, which can be applied to a terminal or a server. The terminal can be but not limited to various personal computers, notebook computers, smart phones, tablet computers and portable intelligent devices, and the server can be realized by an independent server or a server cluster composed of multiple servers. The method includes the following steps:

Step 101, obtain a drug ligand training set, and the drug ligand training set includes a drug ligand chemical formula and a classification label.

The server can obtain a drug ligand training set, and the drug ligand training set contains the drug ligand chemical formula and the classification label. Pharmacologically, receptors refer to biological macromolecules composed of glycoproteins or lipoproteins, which exist in cell membrane, cytoplasm or nucleus. Different receptors have specific structures and configurations.

A receptor is a molecule on the cell surface or in subcellular components, which can recognize and specifically bine to a biologically active chemical signal substance (ligand), thereby activating or initiating a series of biochemical reactions, and finally leading to the specific biological effect of the signal substance. Ligand refers to a substance that can recognize the receptor and bind to it, that is, a drug. The drug ligands in the drug ligand training set can be already validated drug ligands. The classification label can be words or letters that describe the properties of the drug ligand, or the content related to the receptor.

Step 102, based on the ligand chemical formula, a ligand graph network is drawn, in which atoms are nodes and chemical bonds are edges connecting nodes.

The server based on the ligand chemical formula draws a ligand graph network, in which the atoms are nodes and the chemical bonds are the edges connecting the nodes. When there is a chemical bond between two atoms, whether the bond is a single, a double bond or a triple bond, it is drawn as an edge. The ligand graph network can be a set of functions organized in a topological space according to graph structure for relational reasoning. The graph structure can be composed of two sets: Node set (Node) and Edge set (Edge), where the edge set describes how nodes are connected to each other.

Step 103, use a random initialization vector to identify the weight vector of each node in the ligand graph network.

The server uses random initialization vector to identify the weight vector of each node in the ligand graph network. The server can randomly generate the weight value of any edge, and then assign the corresponding weight vector to each node according to the generated weight value. In one of the embodiments, using random initialization vector to identify the weight vector of each node in the ligand graph network includes: using uniform distribution or normal distribution to select the value of (0,1) interval to generate initialization vector, and assigning it to the node as its weight vector. For example, the server can assign the weight value to each edge in a uniform distribution way, and then assign the corresponding weight vector to each node according to the generated weight value. Uniform distribution means that each value in the pointing quantity is distributed in the interval of (0,1) with equal probability. Normal distribution refers to each value of the vector is normally distribution in the interval of (0,1).

Step 104, reconstruct each node of the ligand graph network according to the connection relationship of the ligand graph network to obtain a reconstruction network, and repeat the reconstruction steps to obtain at least two layers of reconstruction networks.

The server reconstructs each node of the ligand graph network according to the connection relationship of the ligand graph network to obtain a reconstruction graph network, and repeat the reconstruction steps to obtain at least two layers of reconstruction graph networks.

Preferably, the number of layers of the server reconstruction graph network is 3 to 6 layers. The server repeats the reconstruction steps each time based on the newly-constructed reconstruction graph network, so each reconstruction graph network is different, and the information contained in each node is gradually enriched.

Step 105, perform deep learning on the ligand graph network and the at least two-layer reconstruction graph network according to the classification labels, and construct a ligand screening model.

The server performs deep learning on the ligand graph network and the at least two-layer reconstruction graph network according to the classification labels, and constructs a ligand screening model. The deep learning network can be BP neural network (Back Propagation), convolutional network, neural network, etc. The server determines the network features in the ligand graph network and the at least two-layer reconstruction graph network through the learning network, and the network features are trained to correspond to the classification labels to construct and obtain a ligand screening model.

In the above method, the ligand graph network corresponding to the ligand chemical formula is modeled and analyzed, and the ligand graph network and the reconstruction graph network are adopted in modeling instead of the traditional method based on molecular fingerprint (Fingerprint), and only two different graph networks of the same ligand are identified by machine learning, which can not only effectively reduce artificial feature design, but also expand the coverage of features, improve efficiency and accuracy, and greatly save molecular dynamics, quantum mechanics and quantum learning by using big data and deep learning methods. The invention can better simulate the structural diversity of small molecules in different physiological environments, and accurately predict the properties of compounds in biological and chemical experiments of different scales.

As shown in FIG. 2, in one embodiment, reconstruct each node of the ligand graph network according to the connection relationship of the ligand graph network to obtain a reconstruction graph network, which includes the following steps:

Step 201, obtain the weight vector of each node and the associated weight vector of the associated node connected with the node according to the connection relationship of the ligand graph network.

The server obtains the weight vector of each node and an associated weight vector of the associated node connected with the node according to the connection relationship of the ligand graph network.

Step 202, the weight vector and the associated weight vector are integrated to obtain the reconstruction weight vector of the node.

The server integrates the weight vector and the associated weight vector to obtain the reconstruction weight vector of the node. In one embodiment, the integration formula is $\vec{h}_i^{k+1} = \Sigma_{v_j \in N(v_i)} f^k(\vec{h}_i^k, \vec{h}_j^k, \vec{e}_{ij})$, where is the set of nodes connecting all nodes i, $v_i$ is the ith node, i, j are the node numbers, $\vec{h}_i^k, \vec{h}_j^k$ is the vector of the nodes numbered i and j in the kth layer network, and $\vec{e}_{ij}$ is the vector of the edge, $f^k$ is the kth layer network.

Step 203, Generate a reconstruction graph network according to the reconstruction weight vector.

The server generates a reconstruction graph network according to the reconstruction weight vector.

In one embodiment, the ligand graph network and at least two layers of reconstruction graph networks are deeply learned according to the classification labels, and construct a ligand screening model, which includes: respectively extracting the features of the ligand graph network and the at least two layers of reconstruction graph networks to obtain hierarchical network features; According to the classification label, a deep learning network is adopted to learn the hierarchical network characteristics, and construct a ligand screening model.

The server performs feature extraction on the ligand graph network and the at least two-layer reconstruction graph network, respectively, to obtain hierarchical network features. In one embodiment, the server may extract the picture features of the ligand graph network and the reconstruction graph network respectively, and analyze the picture details in the graph network. In one embodiment, the server may extract the vector features of the ligand graph network and the reconstruction graph network respectively, and then analyze the graph network. Specifically, the server can follow the formula, $\vec{h}_G = R(\{\vec{h}_v^k | v \in G\})$, where R is the readout function (feature read function). The server can select vector features by adding and averaging.

In one of the embodiments, feature extraction is performed on the ligand graph network and the at least two-layer reconstruction graph network respectively to obtain hierarchical network features, including: performing feature extraction on the ligand graph network and the at least two layers of the reconstruction graph network respectively through a function to obtain function vector features; The function vector features are normalized in probability space to obtain hierarchical network features.

The server performs feature extraction on the ligand graph network and the at least two-layer reconstruction graph network respectively through functions to obtain function vector features.

The server obtains the function vector feature according to the formula, $\vec{h}_G = R(\{\vec{h}_v^k | v \in G\})$, where R is the readout function (feature read function). The server selects vector features by taking an average. The server normalizes the function vector features in the probability space to obtain hierarchical network features. The server can take the softmax function as a direct function of the classifier and compute the normalization operation in the probability space. The specific mathematical formula of the softmax function is $$\text{softmax}(z_i) = \frac{e^{z_i}}{\sum_{j=1}^{n} e^{z_j}},$$

and its function is to normalize the calculated result from the entire real number field to the (0, 1) interval, thereby representing the probability between each node.

The above method only retains the most core compound information (such as atomic number, single or double bonds and other node or edge information) as the connected atom information, so that model training can be completed more efficiently and high-quality models can be extracted.

The application also provides a drug ligand screening method, including:

Drawing a target ligand graph network based on the ligand chemical formula of the target ligand, in which atoms are nodes and chemical bonds are edges connecting the nodes;

Input the target ligand graph network into the ligand screening model, and output the analysis result of the target ligand, wherein the ligand screening model is trained by the above method.

In one embodiment, as shown in FIG. 3, a ligand screening model construction device is provided, which includes a training set acquisition module 301, a graph network drawing module 302, a vector identification module 303, a reconstruction module 304 and a model training module 305.

A training set acquisition module 301, configured to acquire a drug ligand training set, wherein the drug ligand training set includes a drug ligand chemical formula and a classification label.

The network drawing module 302 is used to draw a ligand graph network based on the ligand chemical formula, in which atoms are nodes and chemical bonds are edges connecting nodes.

The vector identification module 303 is configured to identify the weight vector of each node in the ligand graph network by using a random initialization vector.

The reconstruction module 304 is used to reconstruct each node of the ligand graph network according to the connection relationship of the ligand graph network to obtain a reconstruction graph network, and repeating the reconstruction steps to obtain at least two layers of reconstruction networks.

The model training module 305 is used for deeply learning the ligand graph network and at least two layers of reconstruction graph networks according to the classification labels, and construct a ligand screening model.

In one embodiment, the vector identification module includes:

The vector identification unit is used to select values in the (0,1) interval using uniform distribution or normal distribution to generate an initialization vector, and assign it to nodes as its weight vector.

In one embodiment, the reconstruction module 304 includes:

The weight vector obtaining unit is used to obtain the weight vector of each node and the associated weight vector of the associated node connected to the node according to the connection relationship of the ligand graph network.

The integration unit is used to integrate the weight vector and the associated weight vector to obtain the reconstruction weight vector of the node.

The reconstruction unit is used to generate a reconstruction graph network according to the reconstruction weight vector.

In one of the embodiments, the model training module includes:

The feature extraction unit is used to respectively extract features of the ligand graph network and at least two layers of reconstruction graph networks to obtain hierarchical network features.

The model building unit is used to learn hierarchical network characteristics by adopting deep learning network according to the classification labels, and building a ligand screening model.

In one of the embodiments, the model training module includes:

The vector extraction unit is used to respectively extract the features of the ligand graph network and the at least two layers of reconstruction graph networks through functions to obtain the function vector features.

The normalization unit is used to normalize the feature of the function vector in the probability space to obtain the hierarchical network feature.

In one embodiment, a ligand screening device is provided, which includes a graph network drawing module and a ligand analysis module.

The network drawing module is used to draw a target ligand graph network based on the ligand chemical formula of the target ligand, in which atoms are nodes and chemical bonds are edges connecting the nodes.

The ligand analysis module is used to input the target ligand graph network into the ligand screening model and output the analysis result of the target ligand, wherein the ligand screening model is obtained by training by the above method.

Figure 4:
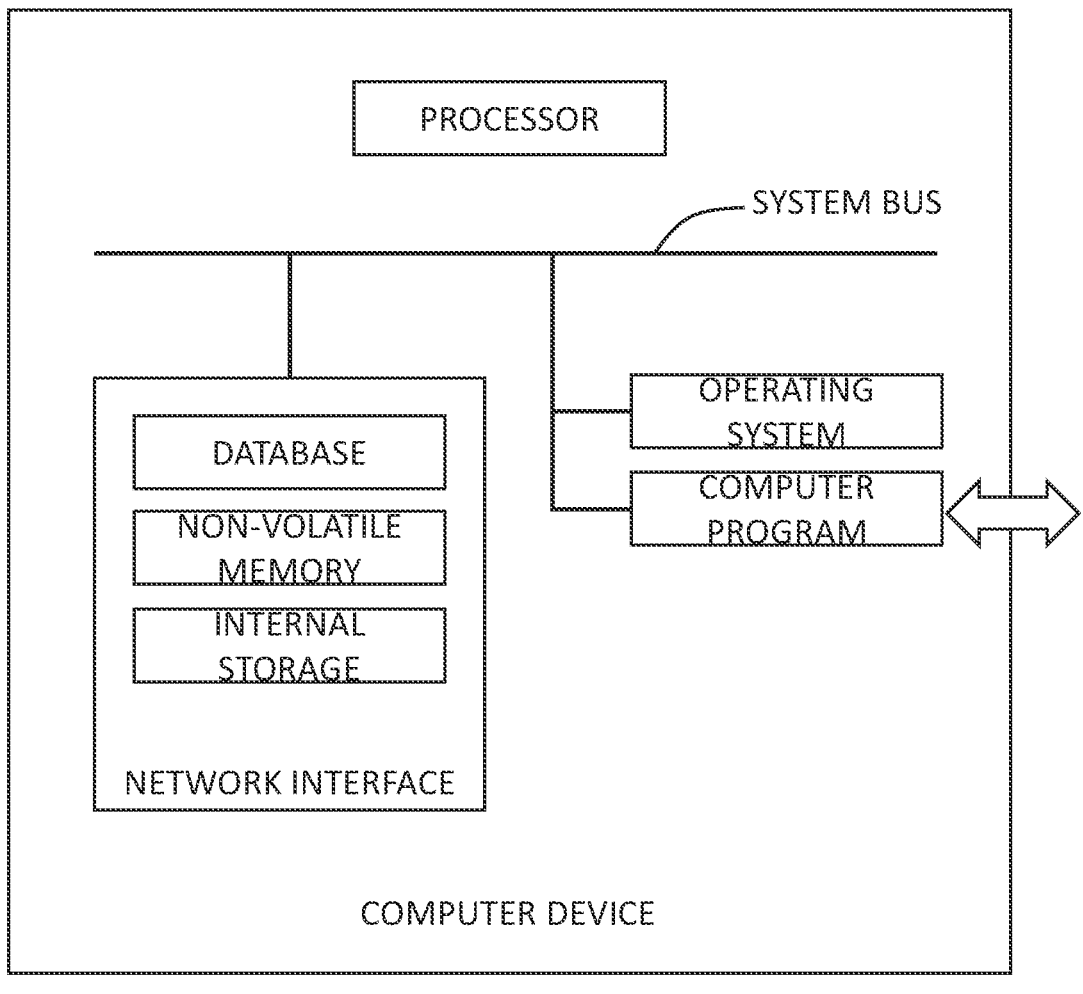
FIG. 4 is an internal structure diagram of a computer device in an embodiment of the present invention.

In one embodiment, a computer device is provided, and the computer device may be a server, and its internal structure diagram may be as shown in FIG. 4. The computer device includes a processor, memory, a network interface, and a database connected by a system bus. Wherein, the processor of the computer device is used to provide computing and control capabilities. The memory of the computer device includes a nonvolatile storage medium, an internal memory. The nonvolatile storage medium stores an operating system, a computer program, and a database. The internal memory provides an environment for the operation of the operating system and computer programs in the non-volatile storage medium. The database of the computer device is used to store data such as a drug ligand training set or a ligand screening model. The network interface of the computer device is used to communicate with an external terminal through a network connection. The computer program, when executed by the processor, realizes a ligand screening model construction method or a drug ligand screening method.

In one embodiment, a computer device is provided, including a memory and a processor, the memory stores a computer program, and when the processor executes the computer program, the processor implements the following steps: obtain a drug ligand training set, where the drug ligand training set includes drug ligand chemical formula and classification label; based on ligand chemical formula, draw a ligand graph network, in which atoms are nodes, and chemical bonds are edges connecting nodes; random initialization vector is used to identify the weight of each node in the ligand graph network vector; reconstruct each node of the ligand graph network according to the connection relationship of the ligand graph network to obtain a reconstruction graph network, and repeat the reconstruction steps to obtain at least two layers of reconstruction graph networks; according to the classification labels, the ligand graph network and at least a two-layer reconstruction graph network are deep learned, and construct a ligand screening model.

In one embodiment, when the processor executes the computer program, using a random initialization vector to identify the weight vector of each node in the ligand graph network includes: select the value of (0,1) interval by uniform distribution or normal distribution to generate the initialization vector, and assign it to the node as its weight vector.

In one embodiment, when a processor executes a computer program, reconstructing each node of the ligand graph network according to the connection relationship of the ligand graph network to obtain a reconstruction graph network, which includes: obtain the weight vector of each node and the associated weight vector of the associated node connected with the node according to the connection relationship of the ligand graph network; integrate the weight vector with the associated weight vector to obtain the reconstruction weight vector of the node; generate the reconstruction graph network according to the reconstruction weight vector.

In one embodiment, when the processor executes the computer program, performing deep learning on the ligand graph network and the at least two-layer reconstruction graph network according to the classification labels, and constructing the ligand screening model, includes: respectively extract features of the ligand graph network and at least two layers of the reconstruction graph network to obtain the hierarchical network features; according to the classification labels, the deep learning network is used to learn the hierarchical network features, and construct a ligand screening model.

In one embodiment, when the processor executes the computer program, the feature extraction is performed on the ligand graph network and the at least two-layer reconstruction graph network, respectively, to obtain hierarchical network features, including: feature extraction is performed on the ligand graph network and at least two layers of reconstruction graph networks by functions to obtain function vector features; the function vector features are normalized in the probability space to obtain hierarchical network features.

In one embodiment, a computer device is provided, including a memory and a processor, the memory stores a computer program, and the processor implements the following steps when executing the computer program: drawing the target ligand graph network based on the ligand chemical formula of the target ligand, the atoms in the ligand graph network are nodes, and the chemical bonds are the edges connecting the nodes; input the target ligand graph network into the ligand screening model, and output the analysis results of the target ligand, wherein the ligand screening model is obtained by training by the above-mentioned method.

In one embodiment, a computer-readable storage medium is provided, on which a computer program is stored, and when the computer program is executed by a processor, the following steps are implemented: obtain a drug ligand training set, where the drug ligand training set includes drug ligands chemical formula and classification label; based on the chemical formula of the ligand, draw a ligand graph network, the atoms in the ligand graph network are nodes, and the chemical bonds are the edges connecting the nodes; the random initialization vector is used to identify the weight vector of each node in the ligand graph network; according to the connection relationship of the ligand graph network reconstructs each node of the ligand graph network to obtain a reconstruction graph network, and repeats the reconstruction steps to obtain at least two layers of the reconstruction graph network; according to the classification labels, the ligand graph network and at least a two-layer reconstruction graph network are deep learned, and construct a ligand screening model.

In one embodiment, when the computer program is executed by the processor, using a random initialization vector to identify the weight vector of each node in the ligand graph network includes: select the value of (0,1) interval by uniform distribution or normal distribution to generate the initialization vector, and assign it to the node as its weight vector.

In one embodiment, when the computer program is executed by the processor, reconstructing each node of the ligand graph network according to the connection relationship of the ligand graph network to obtain a reconstruction graph network, which includes: obtain the weight vector of each node and the associated weight vector of the associated node connected with the node according to the connection relationship of the ligand graph network; integrate the weight vector with the associated weight vector to obtain the reconstruction weight vector of the node; generate the reconstruction graph network according to the reconstruction weight vector.

In one embodiment, when the computer program is executed by the processor, performing deep learning on the ligand graph network and the at least two-layer reconstruction graph network according to the classification labels, and constructing the ligand screening model, includes: respectively extract features of the ligand graph network and at least two layers of the reconstruction graph network to obtain the hierarchical network features; according to the classification labels, the deep learning network is used to learn the hierarchical network features, and construct a ligand screening model.

In one embodiment, when the computer program is executed by the processor, the feature extraction is performed on the ligand graph network and the at least two-layer reconstruction graph network, respectively, to obtain hierarchical network features, including: feature extraction is performed on the ligand graph network and at least two layers of reconstruction graph networks by functions to obtain function vector features; the function vector features are normalized in the probability space to obtain hierarchical network features.

In one embodiment, a computer-readable storage medium is provided on which a computer program is stored, and the computer program implement the following steps when executed by a processor: drawing the target ligand graph network based on the ligand chemical formula of the target ligand, the atoms in the ligand graph network are nodes, and the chemical bonds are the edges connecting the nodes; input the target ligand graph network into the ligand screening model, and output the analysis results of the target ligand, wherein the ligand screening model is obtained by training by the above-mentioned method.

The embodiments described herein are only specific embodiments of the present application, and are not intended to limit the protection scope of the present application. Any modification or equivalent that can be easily conceived by persons skilled in the art should all fall within the protection scope of the present application. Therefore, the protection scope of the present disclosure is subject to the protection scope of the claims.

We claim:

1. A ligand screening model construction method, which comprises:

obtaining a drug ligand training set, wherein the drug ligand training set includes a drug ligand chemical formula and one or more classification labels;

based on the ligand chemical formula, drawing a ligand graph network, in which atoms are nodes and chemical bonds are edges connecting the nodes;

using a random initialization vector to identify a weight vector of each node in the ligand graph network;

reconstructing each node of the ligand graph network according to a connection relationship of the ligand graph network to obtain a reconstruction graph network, and repeating the reconstruction step to obtain a reconstruction graph network comprising at least two layers;

performing deep learning on the ligand graph network and the reconstruction graph network comprising at least two layers, according to one or more classification labels; and constructing a ligand screening model.

2. The method according to claim 1, wherein using a random initialization vector to identify the weight vector of each node in the ligand graph network includes:

using at least one of a uniform distribution model and a normal distribution model to select a value of a $(0,1)$ interval to generate the initialization vector; and assigning the initialization vector to the node as the weight vector.

3. The method according to claim 1, wherein reconstructing each node of the ligand graph network according to the connection relationship of the ligand graph network to obtain a reconstruction network includes:

obtaining the weight vector of each node and an associated weight vector of an associated node connected with the node according to the connection relationship of the ligand graph network;

integrating the weight vector and the associated weight vector together to obtain a reconstruction weight vector of the node; and generating the reconstruction network according to the reconstruction weight vector.

4. The method according to claim 1, wherein the ligand graph network and the reconstruction graph network comprising at least two layers are deeply learned according to the classification labels; and further comprising:

constructing a ligand screening model, which includes:

respectively extracting features of the ligand graph network and the reconstruction graph network comprising at least two layers, to obtain hierarchical network features;

according to the classification label, adopting a deep learning network to learn hierarchical network characteristics; and constructing the ligand screening model.

5. The method according to claim 4, wherein extracting features is performed on the ligand graph network and the reconstruction graph network comprising at least two layers respectively to obtain hierarchical network features, including:

performing feature extraction on the ligand graph network and the reconstruction graph network comprising at least two layers respectively through a function to obtain function vector features; and normalizing the function vector features in probability space to obtain hierarchical network features.

6. A screening drug ligands method, comprising:

drawing a target ligand graph network based on a ligand chemical formula of the target ligand, in which atoms are nodes and chemical bonds are edges connecting the nodes;

inputting the target ligand graph network into a ligand screening model; and outputting an analysis result of the target ligand, wherein the ligand screening model is trained by a method comprising:

a ligand screening model construction method, which comprises:

obtaining a drug ligand training set, wherein the drug ligand training set includes a drug ligand chemical formula and one or more classification labels;

based on the ligand chemical formula, drawing the ligand graph network, in which atoms are nodes and chemical bonds are edges connecting the nodes;

using a random initialization vector to identify a weight vector of each node in the ligand graph network;

reconstructing each node of the ligand graph network according to a connection relationship of the ligand graph network to obtain a reconstruction graph network, and repeating the reconstruction step to obtain a reconstruction graph network comprising at least two layers;

performing deep learning on the ligand graph network and the reconstruction graph network comprising at least two layers, according to one or more classification labels; and constructing the ligand screening model.

7. A ligand screening model construction device, characterized in that the device comprises:

a training set acquisition module, configured to acquire a drug ligand training set, wherein the drug ligand training set includes a drug ligand chemical formula and a classification label;

a network drawing module is used to draw a ligand graph network based on the ligand chemical formula, in which atoms are nodes and chemical bonds are edges connecting nodes;

a vector identification module configured to identify a weight vector of each node in the ligand graph network by using a random initialization vector;

a reconstruction module used to reconstruct each node of the ligand graph network according to a connection relationship of the ligand graph network to obtain a reconstruction graph network, and repeating the reconstruction steps to obtain a reconstruction graph network comprising at least two layers; and a model training module used for deeply learning the ligand graph network and the reconstruction graph network comprising at least two layers, according to the classification labels and construct a ligand screening model.

8. A computer device comprising a memory and a processor, wherein the memory stores a computer program, and is characterized in that when executing the computer program, the processor implements steps of a method comprising:

a ligand screening model construction method, which comprises:

obtaining a drug ligand training set, wherein the drug ligand training set includes a drug ligand chemical formula and one or more classification labels;

based on the ligand chemical formula, drawing a ligand graph network, in which atoms are nodes and chemical bonds are edges connecting the nodes;

using a random initialization vector to identify a weight vector of each node in the ligand graph network;

reconstructing each node of the ligand graph network according to a connection relationship of the ligand graph network to obtain a reconstruction graph network, and repeating the reconstruction step to obtain a reconstruction graph network comprising at least two layers;

performing deep learning on the ligand graph network and the reconstruction graph network comprising at least two layers, according to one or more classification labels; and constructing the ligand screening model.

9. The method according to claim 8, wherein using a random initialization vector to identify the weight vector of each node in the ligand graph network includes:

using at least one of a uniform distribution model and a normal distribution model to select a value of a (0,1) interval to generate the initialization vector; and assigning the initialization vector to the node as the weight vector.

10. The method according to claim 8, wherein reconstructing each node of the ligand graph network according to the connection relationship of the ligand graph network to obtain a reconstruction network includes:

obtaining the weight vector of each node and an associated weight vector of an associated node connected with the node according to the connection relationship of the ligand graph network;

integrating the weight vector and the associated weight vector together to obtain a reconstruction weight vector of the node; and generating the reconstruction network according to the reconstruction weight vector.

11. The method according to claim 8, wherein the ligand graph network and the reconstruction graph network comprising at least two layers are deeply learned according to the classification labels; and further comprising:

constructing a ligand screening model, which includes:

respectively extracting features of the ligand graph network and the reconstruction graph network comprising at least two layers, to obtain hierarchical network features;

according to the classification label, adopting a deep learning network to learn hierarchical network characteristics; and constructing the ligand screening model.

12. The method according to claim 11, wherein extracting features is performed on the ligand graph network and the reconstruction graph network comprising at least two layers respectively to obtain hierarchical network features, including:

performing feature extraction on the ligand graph network and the reconstruction graph network comprising at least two layers respectively through a function to obtain function vector features; and normalizing the function vector features in probability space to obtain hierarchical network features.

13. A non-transitory computer readable storage medium on which a computer program is stored, is characterized in that when a processor executes the computer program, implementing the steps of a method comprising:

a ligand screening model construction method, which comprises:

obtaining a drug ligand training set, wherein the drug ligand training set includes a drug ligand chemical formula and one or more classification labels;

based on the ligand chemical formula, drawing a ligand graph network, in which atoms are nodes and chemical bonds are edges connecting the nodes;

using a random initialization vector to identify a weight vector of each node in the ligand graph network;

reconstructing each node of the ligand graph network according to a connection relationship of the ligand graph network to obtain a reconstruction graph network, and repeating the reconstruction step to obtain a reconstruction graph network comprising at least two layers;

performing deep learning on the ligand graph network and the reconstruction graph network comprising at least two layers, according to one or more classification labels; and constructing the ligand screening model.

14. The non-transitory computer readable storage medium of claim 13, wherein using a random initialization vector to identify the weight vector of each node in the ligand graph network includes:

using at least one of a uniform distribution model and a normal distribution model to select a value of a (0,1) interval to generate the initialization vector; and assigning the initialization vector to the node as the weight vector.

15. The non-transitory computer readable storage medium of claim 13, wherein reconstructing each node of the ligand graph network according to the connection relationship of the ligand graph network to obtain a reconstruction network includes:

obtaining the weight vector of each node and an associated weight vector of an associated node connected with the node according to the connection relationship of the ligand graph network;

integrating the weight vector and the associated weight vector together to obtain a reconstruction weight vector of the node; and generating the reconstruction network according to the reconstruction weight vector.

16. The non-transitory computer readable storage medium of claim 13, wherein the ligand graph network and the reconstruction graph network comprising at least two layers are deeply learned according to the classification labels; and further comprising:

constructing a ligand screening model, which includes:

respectively extracting features of the ligand graph network and the reconstruction graph network comprising at least two layers, to obtain hierarchical network features;

according to the classification label, adopting a deep learning network to learn hierarchical network characteristics; and constructing the ligand screening model.

17. The non-transitory computer readable storage medium of claim 16, wherein extracting features is performed on the ligand graph network and the reconstruction graph network comprising at least two layers respectively to obtain hierarchical network features, including:

performing feature extraction on the ligand graph network and the reconstruction graph network comprising at least two layers respectively through a function to obtain function vector features; and normalizing the function vector features in probability space to obtain hierarchical network features.

* * * * *